(12) United States Patent
Brooke (10) Patent No.: US 11,051,874 B2
(45) Date of Patent: Jul. 6, 2021

(54) ELECTROSURGICAL DEVICE (71) Applicant: Gerard Brooke, Lightpill (GB)

(72) Inventor: Gerard Brooke, Lightpill (GB)

( * ) Notice: Subject to any disclaimer, the term of this patent is extended or adjusted under 35 U.S.C. 154(b) by 0 days.

(21) Appl. No.: 16/366,326

(22) Filed: Mar. 27, 2019

(65) Prior Publication Data

US 2019/0282295 A1 Sep. 19, 2019

Related U.S. Application Data (63) Continuation of application No. 14/888,178, filed as application No. PCT/GB2014/051345 on Apr. 30, 2014, now abandoned.

(30) Foreign Application Priority Data

May 1, 2013 (GB) ..................................... 1307866

(51) Int. Cl.
*A61B 18/14* (2006.01)
*A61B 18/00* (2006.01)
(52) U.S. Cl.
CPC .. *A61B 18/1445* (2013.01); *A61B 2018/0013* (2013.01); *A61B 2018/00101* (2013.01); *A61B 2018/00607* (2013.01); *A61B 2018/1452* (2013.01); *A61B 2218/007* (2013.01)
(58) Field of Classification Search
CPC ............................................. A61B 2018/1462
See application file for complete search history.

(56) References Cited

U.S. PATENT DOCUMENTS

| 853,096 | A | | 5/1907 | Lewis |
|---|---|---|---|---|
| 2,417,530 | A | | 3/1947 | Weiser |
| 3,916,909 | A | | 11/1975 | Kletschka et al. |
| 4,041,952 | A | | 8/1977 | Morrison, Jr. et al. |
| 4,553,021 | A | | 11/1985 | Conti |
| 4,567,890 | A | | 2/1986 | Ohta et al. |
| 5,122,139 | A | * | 6/1992 | Sutter ................ A61B 18/1442 606/51 |

(Continued)

FOREIGN PATENT DOCUMENTS

| EP | 0589453 A2 | 3/1994 |
|---|---|---|
| EP | 0850598 A1 | 7/1998 |

(Continued)

OTHER PUBLICATIONS

PCT International Search Report and Written Opinion, PCT/GB2014/051345, dated Nov. 12, 2014, 13 pages.

(Continued)

*Primary Examiner* — Ronald Hupczey, Jr.
(74) *Attorney, Agent, or Firm* — Quarles & Brady LLP (57) ABSTRACT

A forceps-type electrosurgical device is disclosed comprising, a fixed elongate body and a pair of moveable tips, arranged for engaging tissue in use, and extending from a forward end of the body. The tips are relatively moveable between a first position in which the tips are spaced apart and a second position in which the tips are brought together. The body further comprising an actuation member moveable relative to the body and connected to the tips such that a user may move the actuation member to result in movement of the tips between the first and second positions. The device may further comprise a suction port proximal to the tips.

16 Claims, 7 Drawing Sheets

(56) References Cited

U.S. PATENT DOCUMENTS

| | | | |
|---|---|---|---|
| 5,169,398 A | 12/1992 | Glaros | |
| 5,306,287 A | 4/1994 | Becker | |
| 5,693,052 A * | 12/1997 | Weaver | A61B 18/1442 606/51 |
| 5,752,972 A | 5/1998 | Hoogeboom | |
| 5,797,938 A | 8/1998 | Paraschac et al. | |
| 5,899,900 A * | 5/1999 | Burke | A61B 18/14 606/36 |
| 6,228,084 B1 * | 5/2001 | Kirwan, Jr. | A61B 18/1442 606/51 |
| 6,235,027 B1 * | 5/2001 | Herzon | A61B 18/085 606/28 |
| 6,679,881 B1 * | 1/2004 | Bybee | A61B 18/1442 606/51 |
| 6,750,431 B2 | 6/2004 | Miyazaki | |
| 6,926,717 B1 | 8/2005 | Garito et al. | |
| 8,152,806 B2 * | 4/2012 | Black | A61B 18/1442 606/52 |
| 2004/0098039 A1 | 5/2004 | Sinding | |
| 2006/0122592 A1 | 6/2006 | Treat | |
| 2009/0320268 A1 | 12/2009 | Cunningham et al. | |
| 2011/0288369 A1 | 11/2011 | Ginnebaugh et al. | |

FOREIGN PATENT DOCUMENTS

| | | |
|---|---|---|
| JP | H0197447 A | 4/1989 |
| JP | 2000262533 A | 9/2000 |
| WO | 9624298 A1 | 8/1996 |
| WO | 2006092488 A1 | 9/2006 |
| WO | 2011088387 A2 | 7/2011 |

OTHER PUBLICATIONS

European Patent Office, Communication, Application No. 14725918.8, dated Oct. 5, 2018, 4 pages.
Intellectual Property Office of the United Kingdom, Search Report, Application No. GB1307866.2, dated Oct. 23, 2013, 6 pages.
Intellectual Property Office of the United Kingdom, Examination Report, Application No. GB1307866.2, dated Jul. 13, 2018, 4 pages.
The State Intellectual Property Office of the People's Republic of China, First Office Action and Search Report, Application No. 2014800376889, dated Aug. 10, 2018, 11 pages.
Japan Patent Office, Notice of Reasons for Refusal, Application No. 2016-511129, dated Mar. 13, 2018, 10 pages.

* cited by examiner

ELECTROSURGICAL DEVICE

CROSS-REFERENCE TO RELATED APPLICATIONS

This application is a continuation of U.S. patent application Ser. No. 14/888,178, filed Oct. 30, 2015, which represents the national stage entry of PCT International Application No. PCT/GB2014/051345, filed Apr. 30, 2014, which claims the benefit of Great Britain Patent Application No. 1307866.2 filed on May 1, 2013, the disclosures of which are hereby incorporated by reference in their entirety for all purposes.

FIELD OF THE INVENTION

This invention relates to a forceps-type electrosurgical device in particular, but not exclusively, to an electrosurgical device for use with a high frequency (RF) current.

BACKGROUND OF THE INVENTION

As referred to herein a "forceps-type electrosurgical device" means an electrosurgical device which is suitable for providing the function of electrosurgical forceps.

Electrosurgical forceps comprise a pair of opposed tips which are typically relatively moveable such that they may be may be used to grasp or engage objects such as biological tissue. During electrosurgery a high frequency (RF) electric current is applied using the forceps such that the tips acts as electrodes for passing the ac current into the tissue. Depending upon the properties of the current and the manner in which the forceps engage the tissue electrosurgical forceps may, for example, be used to cut, coagulate, desiccate and/or fulgurate the tissue. In particular, electrosurgical devices are commonly used during surgery in order to stop bleeding by using an alternating current directly heat tissue and thereby reduce blood loss and/or improved surgical vision.

Two primary types of electrosurgical device are known, namely bipolar and monopolar devices.

In monopolar arrangements the electrosurgical device is provided with an active electrode and a return electrode is attached to the patient. The electric current flows from the active electrode into the body and returns through the return electrode (which is connected to an earthing circuit). The current density decreases rapidly with distance away from the electrode such that the heating of tissue is localised to the tip of the electrosurgical device.

In bipolar devices, a pair of electrodes, for example the tips of forceps, are each connected to the supply circuit and no return electrode is required. When tissue is engaged by or proximal to the pair of electrodes, the high frequency electric current flows through the device and tissue providing a localised heating of the tissue.

Conventionally, electrosurgical forceps have a design which is substantially based upon traditional surgical forceps. As such, electrosurgical forceps generally comprise a pair of elongate fingers connected at a rearward hinge such that the forward end of the forceps may be used to grasp or hold objects such as biological tissue. Being based upon traditional non-electrosurgical devices conventional electrosurgical forceps are not typically optimised for use in electrosurgery. Accordingly, it would be desirable to provide a new forceps design which is specifically designed for use in electrosurgery so as to improve ease of use.

SUMMARY OF THE INVENTION

According to a first aspect of the present invention there is provided a forceps type electrosurgical device comprising:

a fixed elongate body;

a pair of moveable tips, arranged for engaging tissue in use and extending from a forward end of the body, the tips being relatively moveable between a first position in which the tips are spaced apart and a second position in which the tips are brought together;

the body further comprising an actuation member moveable relative to the body and connected to the tips such that a user may move the actuation member to result in movement of the tips between the first and second positions It will be appreciated that the relative movement between the tips may be provided by one or both tips being moveably connected to the fixed elongate body.

The moveable tips are typically resiliently biased towards the first position. For example, the moveable tips may be resiliently biased towards the first position by the elongate body. The actuation member may be arranged to urge the tips together against the resilient bias. The body may comprise a spring member arranged to bias the tips towards the first position.

The actuation member may be provided on an outer surface of the elongate body. The actuation member may be inwardly compressible. The actuation member may comprise a pair of finger receding portions provided on opposing sides of the body. For example, one or both of the finger receiving portions may be inwardly moveable relative to the body. Thus, the actuation member may conveniently be actuated by being squeezed between the fingers of an end user.

The forceps may further comprise a suction port proximal to the tips. This is considered novel and inventive in its own right and, accordingly a further aspect of the invention provides an electrosurgical device comprising a pair of moveable tips at a forward end arranged for engaging tissue in use and a suction port proximal to such tips.

The suction port may for example be provided at a forward most portion of the fixed elongate body. A conduit may be provided extending through the fixed elongate body. For example the conduit may extend from a connector at or proximal to the rear of the body for receiving a suction line to the suction port. The suction port may, therefore, be used to draw gas away from the tips through the elongate body of the device. Advantageously, the inclusion of an integral suction port may help to reduce the number of instruments required during a surgical procedure. Further, the provision of suction local to the tips may reduce or limit the release of potentially harmful vapours and/or improve surgical vision.

The electrosurgical device may comprise an electrical switch. The switch may be activated upon movement of the tips, for example the switch may be activated when the tips are moved to the second position. The activation may be automatic. An automatic switch arrangement may be particularly suitable for a bipolar device. The electrical switch may be engaged by a portion of the actuating member. Alternatively, the electrical switch may be engaged by a portion of the tips.

The electrical switch may be disposed between the moveable portions of the actuation member such that it is physically engaged upon movement of the actuation member. For example, the electrical switch may be provided on a fixed portion of the elongate body adjacent to the actuation member such that it is engaged upon movement of the actuation member. Alternatively, the switch may be provided on the actuation member and may be engaged by opposing movement portions of the actuation member. The switch may require a minimal engagement pressure in order to activate (for example to avoid premature or unintentional actuation of the surgical current).

In some embodiments the body may further comprise an electrical activation button on an outer surface thereof. The button may take any conventional form (for example a compression button, a key, a slidable switch or the like). For example, an activation button may be provided on an outer surface of the elongate body or on the outer surface of the actuation member. Such an externally provided activation button may typically be arranged to be physically activated by an end user. The activation button may be arranged such that it is deactivated when the tips are in the first position. For example, the activation button may be spaced apart from an electrical switch (which is operated by the button) until the actuation member is moved relative to the body. Alternatively, the activation button may be electrically isolated until the actuation member is moved relative to the body.

The electrical activation button may be arranged to enable selection between different modes of operation. For example, the switch may enable selection of differing magnitude and/or waveforms of the applied current corresponding to different electrosurgical procedures (for example, cutting or coagulation). Such an arrangement may be particularly suitable for a monopolar surgical device.

At least one of the tips of the electrosurgical device may comprise an outwardly facing surface having a sharp tapered profile. One of the tips may comprise an outwardly facing surface having a blunt profile (such that one tip has a sharp profile and the other has a blunt profile). This arrangement is particularly advantageous since it enables the sharp profile tip to be used during cutting procedures and the blunt tip profile to be used during coagulation procedures.

This arrangement is considered novel and inventive in its own right and therefore according to a further aspect of the invention there is provided an electrosurgical device comprising a pair of tips arranged for engaging tissue in use, the tips being relatively moveable between the first spaced apart position and a second position in which the tips are brought together, wherein one tip comprises an outwardly facing surface with a sharp tip profile and the other tip comprises an outwardly facing surface with a blunt profile.

The tips may comprise inwardly facing opposing planar surfaces. The planar surfaces are generally parallel and spaced apart when the tips are in the first position. The inwardly facing surface may be arranged to abut when the tips are in the second position or may conveniently be used to grip tissue therebetween.

To the rear of the planar surfaces the tips may curve outwardly. The outward curvature may for example be arranged such that the rear portion of the tips are adjacent to an outer portion of the body. This may for example provide a space between the rear portion of the tips to accommodate a suction port.

Alternatively, the tips may taper from a rearward portion towards a point at the forward end.

The fixed elongate body is typically formed from an insulting material. For example, the fixed body may be plastic. The moveable tips may comprise thermally conductive tips. The tips may typically be metallic and may be coated for example the tips may be anodised and/or may be provided with a non stick coating such as Teflon or DLC (diamond like coating). In particular, the tips may be aluminium.

Whilst the invention has been described above extends to any inventive combination of the features set out above or in the following description or drawings.

BRIEF DESCRIPTION OF THE DRAWINGS

A specific embodiment of the invention will now be described in detail, by way of example only, and with reference with the accompanying drawings in which.

DETAILED DESCRIPTION OF EMBODIMENT

Front as used herein will be understood to refer to the end of the forceps (or components thereof) which, in use, are closest to the tissue on which a procedure is being carried out (i.e. the end which is facing the patient). Rear as used herein will be understood to refer to the end of the forceps (or components thereof) which, in use, are furthest from the tissue (i.e. the end which is facing the surgeon). Forward and rearward will, likewise, be understood to refer to the directions orientated towards the front and rear of the forceps.

FIGS. 1 to 4 show a monopolar electrosurgical forceps-type device in accordance with a first embodiment of the invention. The device 1 generally comprises a fixed elongate body 10 having a pair of tips 20 provided at the forward end, a suction port 30 and an actuation member 40 including a button 50. In use, the device 1 is connected to a suction line and RF power supply at a rearward portion.

The body 10 is formed from an elongate and generally cylindrical body which has a pen like profile such that it can be easily gripped by a surgeon during use. A forward portion of the body 12 tapers forwardly towards the tips 20. The body 10 has a substantially hollow profile such that a conduit 34 of a suction port 30 may be defined extending along the length of the body from an inlet 32 adjacent to the tips 20 to a suction line connection 36 at a rearward end 14 of the body 10.

The tips 20a and 20b are movably attached to the body 10 via a pair of flexible arms 44a and 44b of the actuation member 40 (which will be described in further detail below). The tips are connected to the arms by rivets 28 but any convenient fixation means may be used. Each tip 20 comprises a linear forward section 22 and an outwardly curved rearward section 24. The forward sections 22a, 22b extend to a rounded forward end 129 and are provided with opposed planar inwardly facing surfaces faces 23a, 23b which are spaced apart in the open position of FIGS. 1b and 1d and are brought together in the closed position of FIGS. 1a and 1c such that they are generally parallel and abutting (although it will be appreciated that in use the closed position may not always involve the surfaces abutting as shown since tissue may be engaged therebetween). The outwardly curved rearward sections 24 allow the tips 20 to be attached at a radially outwardly position with respect to the body 10. This curved profile provides a spacing between the rearward portions such that the inlet 32 of the suction port 30 may be positioned between the tips (and generally on the axial centre line of the body 10). As will be explained in further detail below (with reference to FIG. 4) the outwardly facing surfaces 26a and 26b of the tips 20a and 20b have non-matching profiles.

The tips 20 are connected to the body 10 via an actuation member 40 which is moveably connected to the body 10. The actuation member 40 comprises a pair of flexible, forwardly extending, arms 44a and 44b. The arms 44a and 44b are formed on opposing sides of the body 10 and are on a radially exterior portion of the body 10. Each arm 44a and 44b is hingedly attached to the body 10 at its rearward end. One of the tips 20a and 20b is rigidly attached to a forward end of each arm 44a and 44b. In the closed position (shown in FIGS. 1b and 1d) the arms 44a and 44b are seated within a pair of recesses 13a and 13b formed at opposing sides of the outer surface of the forward section 12 of the body 10.

The actuation member 40 further comprises two opposing finger receiving portions 42a and 42b which are provided on an outer surface of each arm 44a and 44b in circumferentially opposing positions. The finger receiving portions 42 are shaped and dimensioned so as to be gripped between the fingers (typically the thumb and forefinger in a pinching action) of an end user.

Figures 1A, 1B:
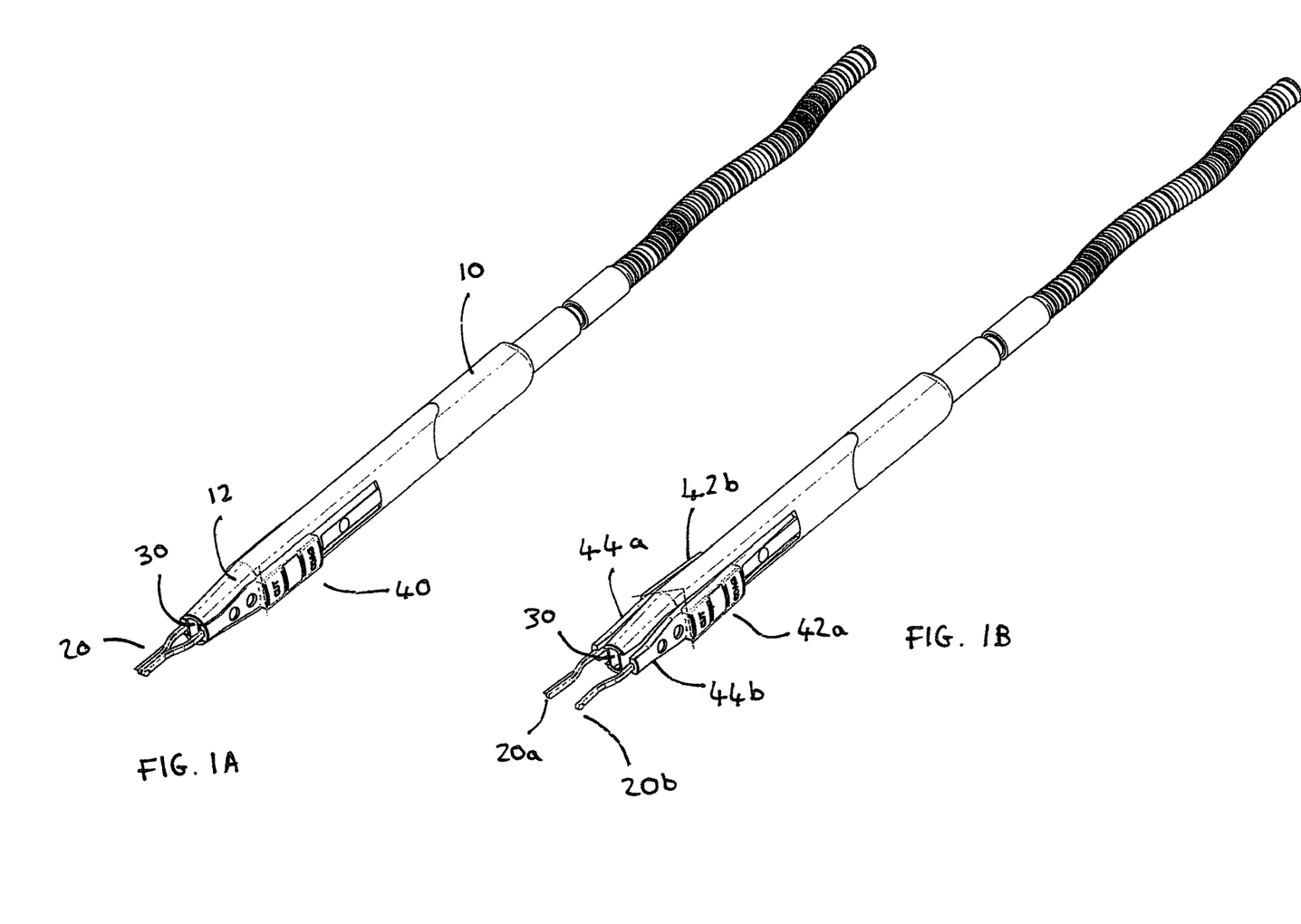
FIG. 1A is a schematic three-dimensional view of a first embodiment of the invention with the tips in an open position.
FIG. 1B is a schematic three-dimensional view of a first embodiment of the invention with the tips in a closed position.
Figure 1C:
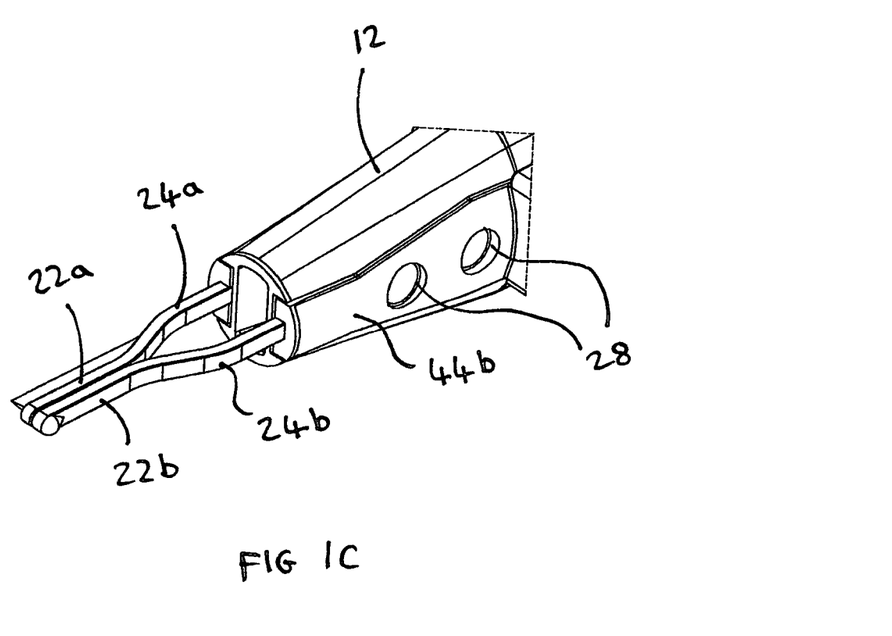
FIG. 1C is a close-up schematic three-dimensional view of a first embodiment of the invention with the tips in an open position.
Figure 1D:
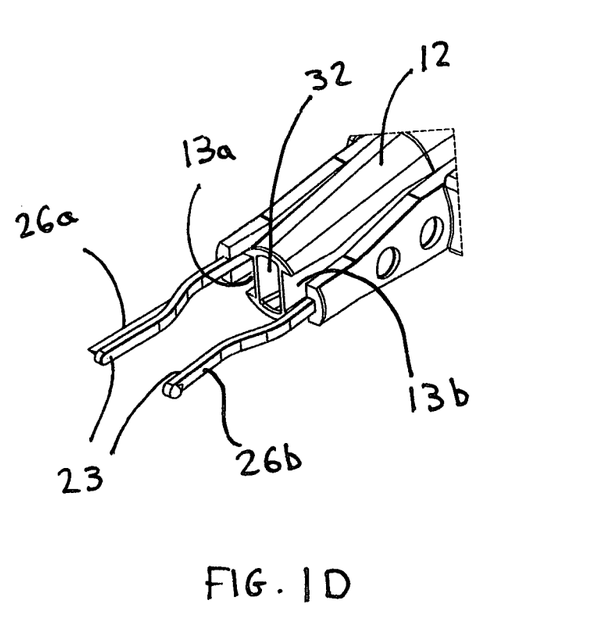
FIG. 1D is a close-up schematic three-dimensional view of a first embodiment of the invention with the tips in a closed position.
Figure 2:
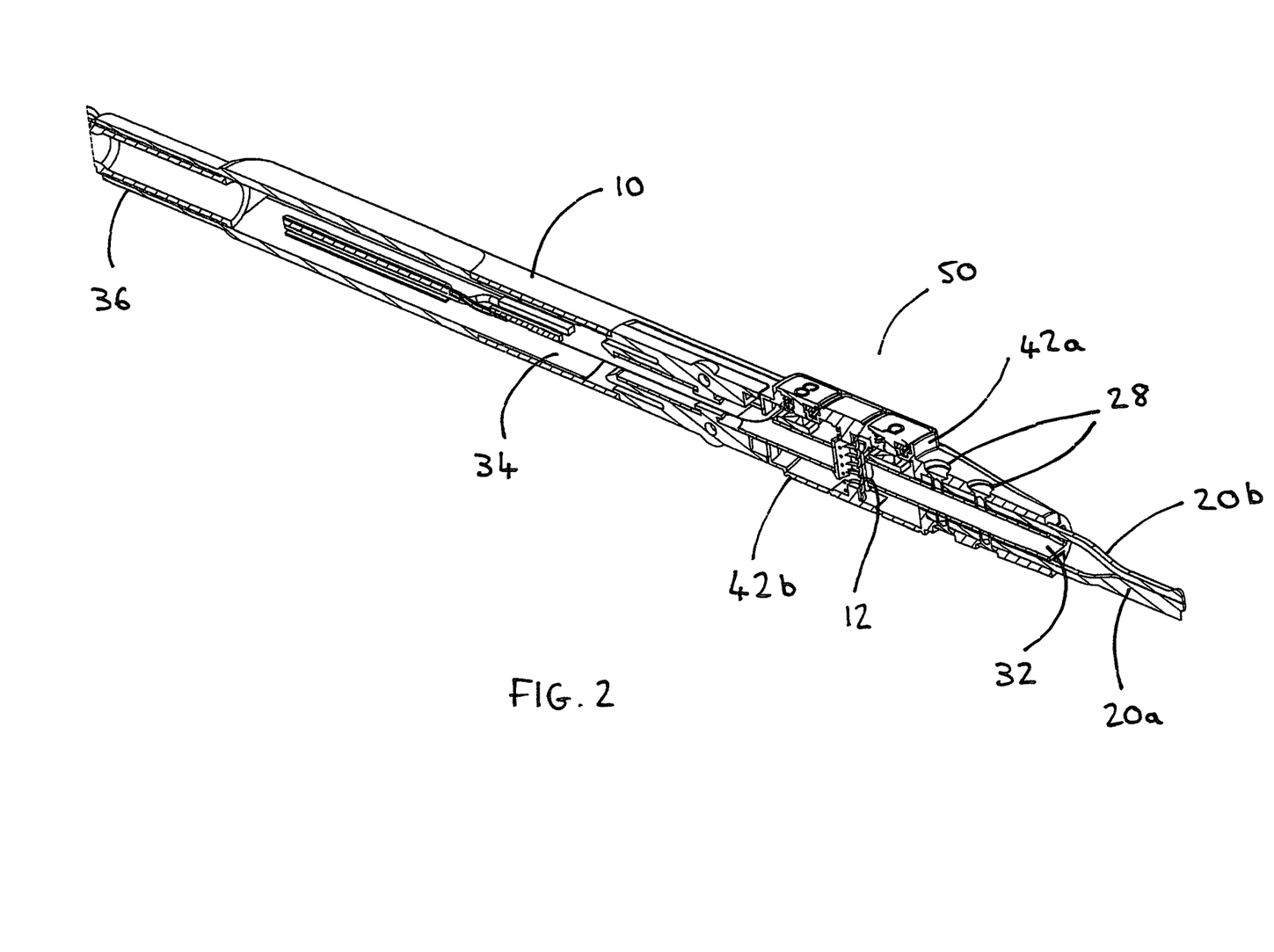
FIG. 2 is a schematic three-dimensional cross-section of the first embodiment.

The body further comprises a spring 12 (by seen in FIGS. 2 and 3) which is disposed between the arms 44a and 44b so as to bias the arms apart and into the open position shown in FIGS. 1b and 1d. Alternatively, the hinged connection between the body 10 and arms 44 may be resiliently outwardly biased (such that inward deflection of the arms 44 is by elastic deformation of the hinged connection or arm).

Figure 3A:
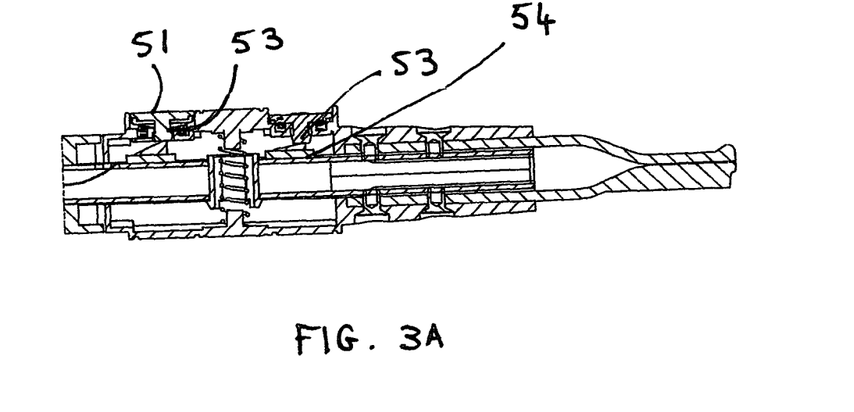
FIG. 3A is a schematic partial cross-section of the forward portion of the first embodiment in an open position.
Figure 3B:
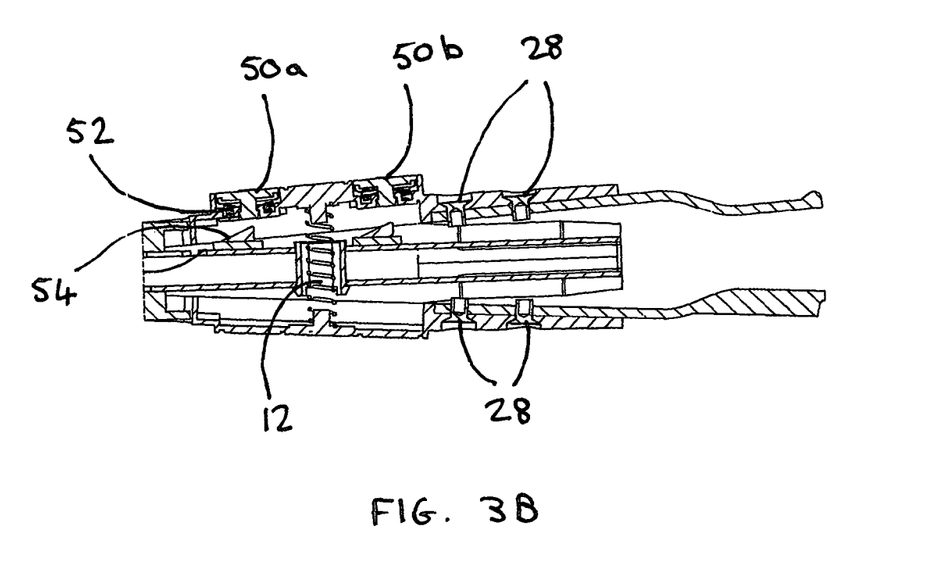
FIG. 3B is a schematic partial cross-section of the forward portion of the first embodiment in a closed position.

As best seen in FIG. 3, a user activation button 50 is provided on the finger receiving portion 42b of one of the arms 44a. The button 50 comprises 50 comprises first button 50a and a second button 50b. Each button is arranged to activate different mode of operation of the forceps (in the illustrated embodiment 50a is activates a "coagulate" mode and 50b activates a "cut" mode). Each button comprises an outer surface 51 which is pressed in use by a user and which is resiliently outwardly biased towards the buttons disengaged position by a spring 52. A shaft 53 projects inwardly from the underside of the surface 51 and is arranged to pass through an aperture 48 in the actuation member 40 when the button 50 is depressed. Typically the shaft 53 may snap fit into the aperture 48 so as to be movably retained therein. The shaft 53 is arranged to engage an underlying electrical activation switch 54 (which may for example be a micro switch or a membrane switch) on the body 10. The switch 54 may for example be formed as part of a PCB. A separate switch 54a and 54b is generally provided for each user activation button 50a and 50b. It may be noted from a comparison of FIGS. 3a and 3b that the relative position of each button 50 and switch 54 and/or the stroke of the shaft 53 is arranged such that the switch 54 can only be engaged by the shaft 53 of the button 50 when the actuation portion 40 is in the position shown in FIG. 3a. In other words, the button 50 is deactivated until the actuation member 40 is moved to bring the tips 20 towards their closed position.

Figure 4A:
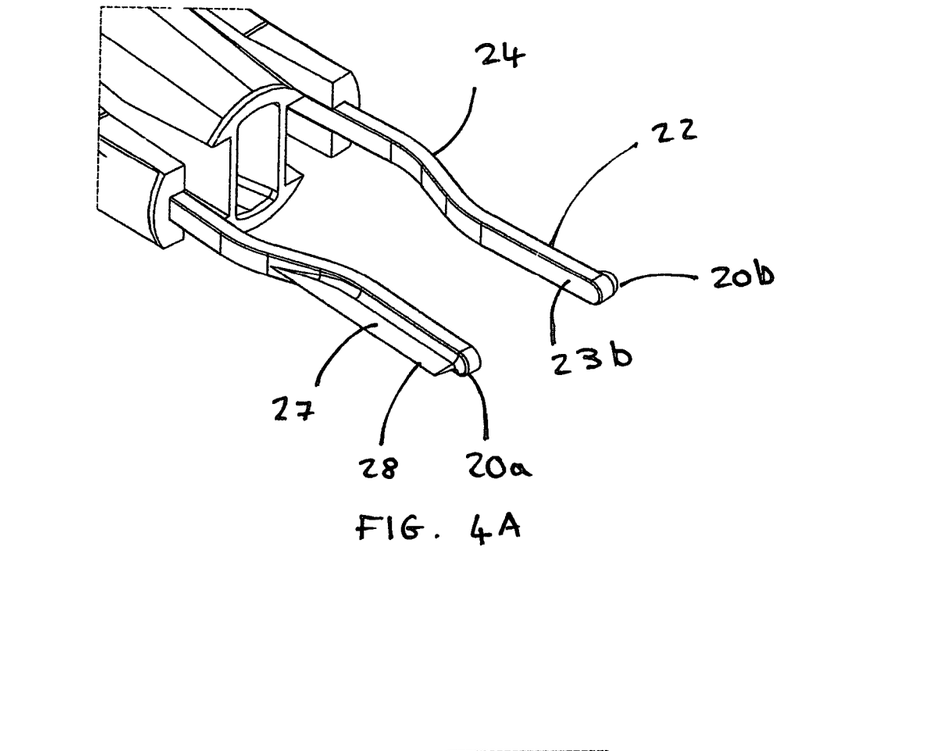
FIG. 4A is a schematic detailed view of the tips for use in an embodiment of the invention from a selected direction.
Figure 4B:
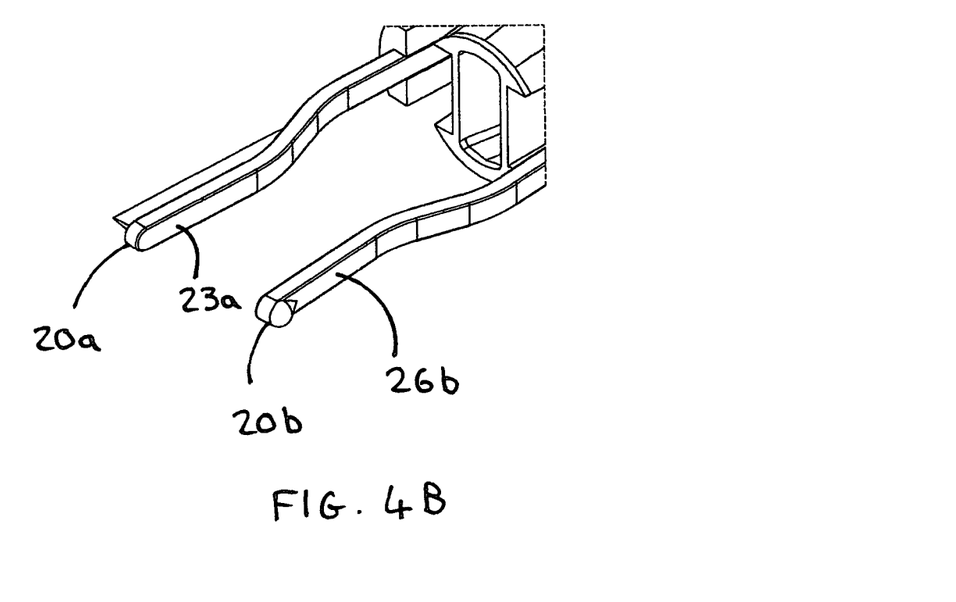
FIG. 4B is a schematic detailed view of the tips for use in an embodiment of the invention from a direction opposite the direction of the view of FIG. 4A.

The profile and function of the tips 20 will now be described in further detail with particular reference to FIG. 4 (in which FIGS. 4a and 4b show views of the same embodiment form opposing directions). As mentioned above, each tip 20 comprises a linear forward section 22 and a curved rearward section 24. The forward section 22 is the "active" section during electrosurgery and the curved section 24 is a connecting portion to the body 10. The forward sections 22a, 22b are provided with opposed planar inwardly facing surfaces faces 23a, 23b which are spaced apart in the open position of FIGS. 1b and 1d and are brought together in the closed position of FIGS. 1b and 1d. One of the tips 20a has an extension 27 which extends axially away from the outward facing surface 26a of the tip 20a and tapers so as to form a relatively sharp edge 28. In contrast, the other tip 20b has an outwardly facing surface 26b which has a rounded and relatively blunt profile.

The provision of surfaces of different profiles improves the utility of the electrosurgical device since each surface may be suitable for different procedures. For example during some procedures tissue may be engaged between the inwardly facing surfaces faces 23a, 23b (for example to weld tissue). In other procedures the tips 20a and 20b may be brought together such that the planar inwardly facing surfaces faces 23a, 23b are abutting and the tips may effectively provide a single electrode. The surgeon may then select to use either the sharp face 26a (e.g. for cutting) or the blunt face 26b (e.g. for coagulating) depending upon the task to be performed. Additionally, the provision of a multiple mode switch 50 allows the surgeon to easily switch between different pre-set profiles of RF current appropriate to the task in hand.

Figure 5:
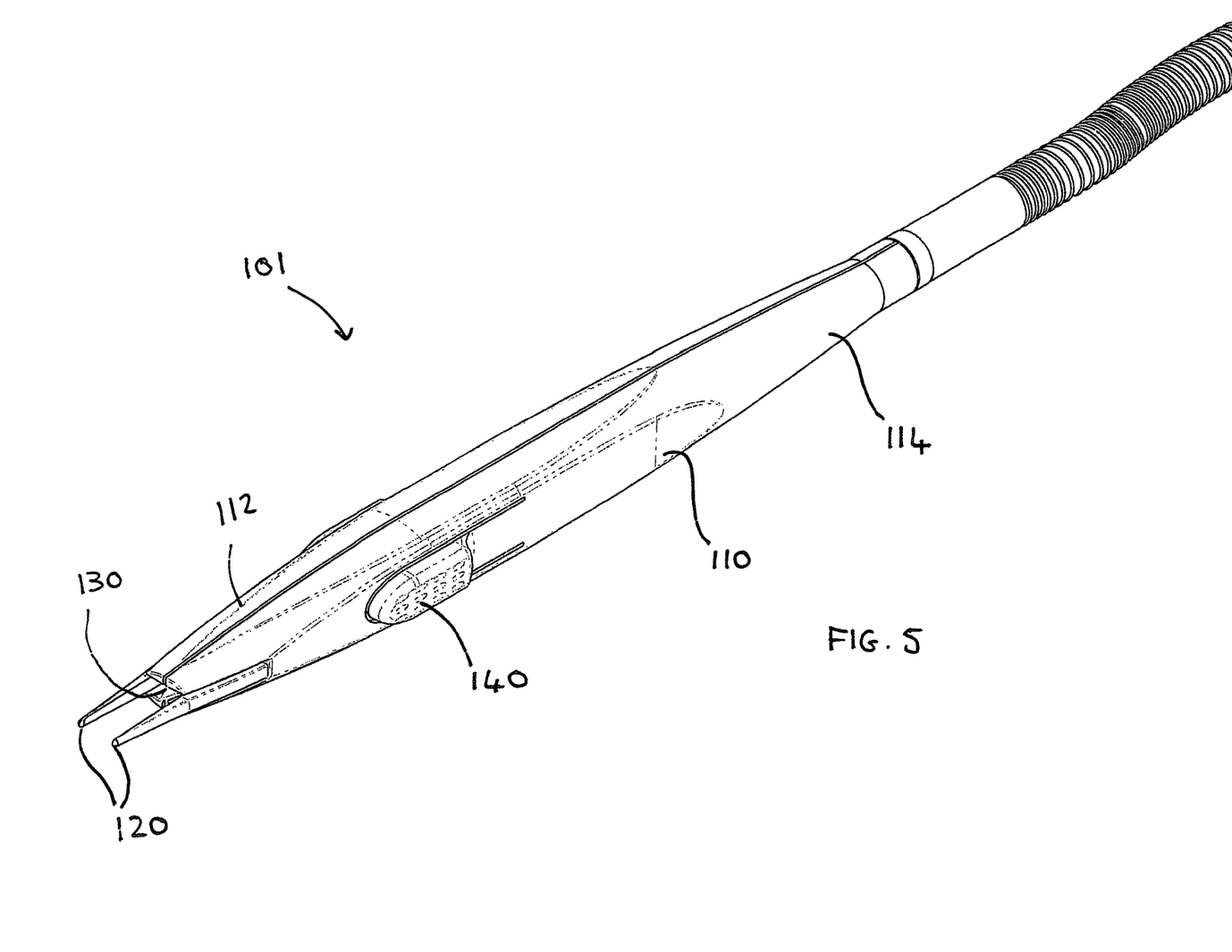
FIG. 5 is a schematic three-dimensional view of a second embodiment of the invention.
Figure 6A:
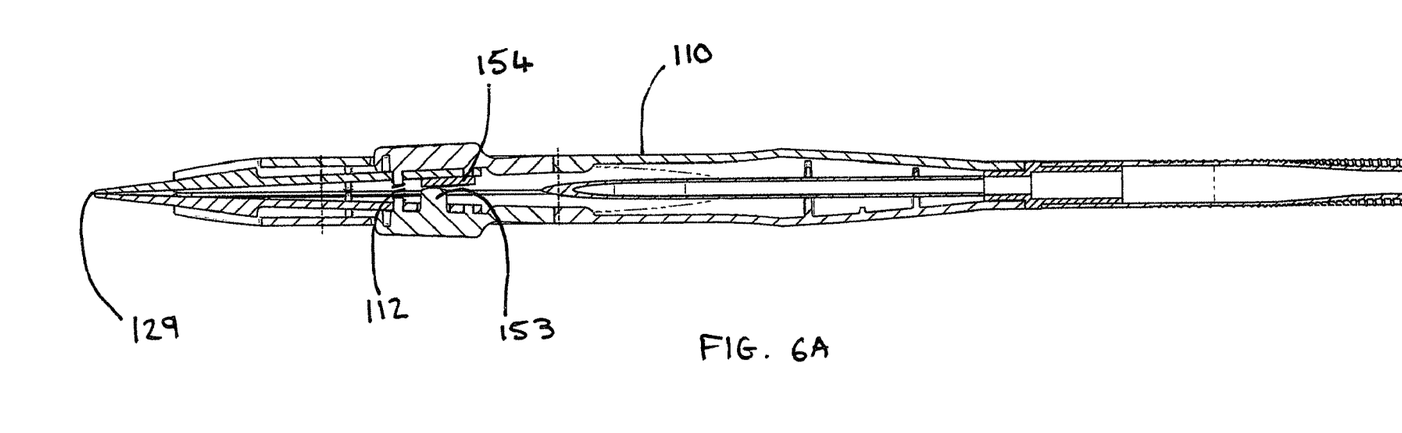
FIG. 6A is a schematic cross-section of the second embodiment in an open position.
Figure 6B:
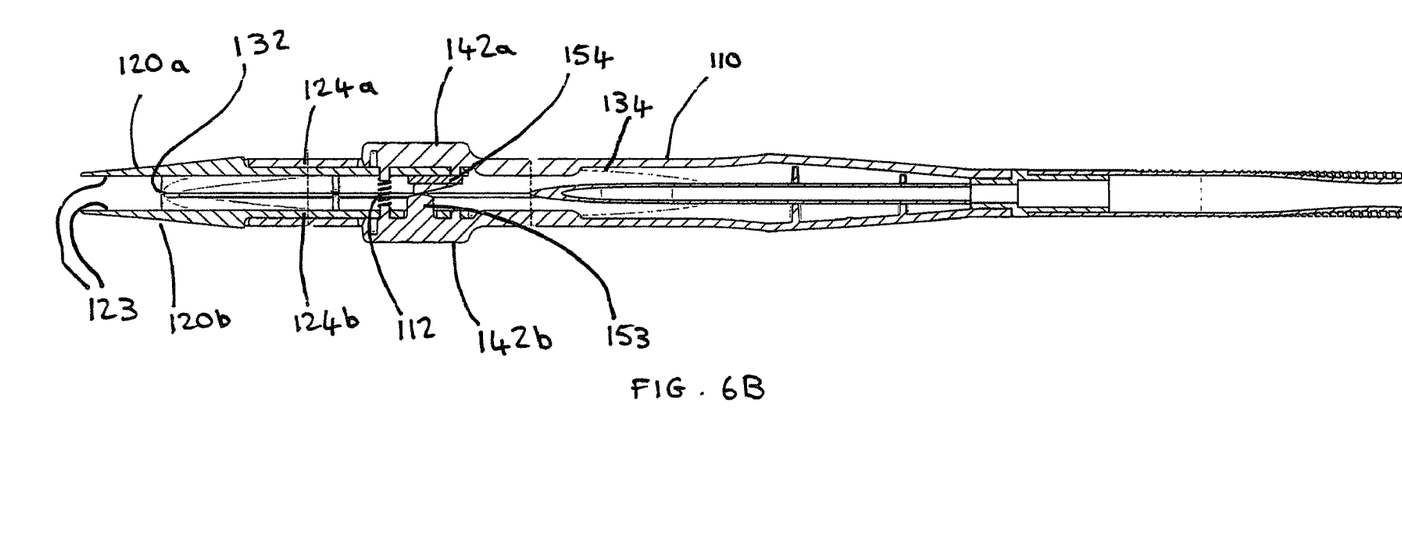
FIG. 6B is a schematic cross-section of the second embodiment in a closed position.

FIGS. 5 and 6 show a bipolar electrosurgical forceps-type device in accordance with a second embodiment of the invention. The general arrangement of the device is similar to that of the first embodiment and corresponding features have been given reference numbers corresponding to those of the first embodiment but increased by 100. The device 101 generally comprises a fixed elongate body 110 having a pair of tips 120 provided at the forward end, a suction port 130 and an actuation member in 140. In use the device 101 is connected to a suction line and RF power supply at a rearward portion of the body 110.

The body 110 is formed from an elongate body which has a pen like profile. A forward portion of the body 112 tapers forwardly towards the tips 120. A rearward portion of the body 114 tapers rearwardly towards a connecting portion for connection to a suction line. The body 110 has a substantially hollow cross section such that a conduit 134 of the suction port 130 may extend along the length of the body from inlet 132 adjacent to tip 120 to a suction line connection 136 at the rearward end 114 of the body 110.

Tips 120a and 120b are moveably attached to the body 110 by the actuation member 140. In contrast to the first embodiment, it may be noted that the tips extend rearwardly beyond the front of the body 110 and into an interior space within the hollow body 110. The rearmost portion of the tips 124 are directly attached to the inward surface of the actuation member 140.

Each of the tips 120a and 120b has a substantially identical profile having a linear (and generally axially extending) inwardly facing surface 123. The forward section 122 of each tip 120 is forwardly tapered such that the end 129 of each tip forms a relatively sharp point. The rearward most portion of the forward section 122 includes an outwardly directed step increase in thickness which is shaped and dimensioned so as to be received into a cut out 113 in the body 110. This cut out 113 enables the forward most portion of the body 110 to extend beyond the forward section 112 of the tips 120 and positions the inlet 132 of the suction port 130 as close to the ends of the tip 120 as possible.

It may also be noted that in contrast to the first embodiment, in the closed position (shown in FIG. 6a) the tips 120a and 120b are not provided with substantially parallel abutting surfaces but meet at a pinch point at the forward most end 129 of the tips 120.

The actuation member 140 comprises a pair of opposing finger receiving portions 142a and 142b which are hingebly connected to the body 110 and which extend from the interior of the body 110 to the outer surface of the device 101. Conveniently, the finger receiving portions 142 are raised from the surface of the body 110 such that they may be easily located and gripped. The outer surface of the finger receiving portions 140 may be provided with a surface profile to assist gripping, for example they may be provided with a plurality of depressions. As the tips 120 are directly connected to the inner surface of the finger receiving portions 142 any inward movement of the actuation member 140 (i.e. by being squeezed between the fingers of an end user) acts to bring the tips 120 together until their ends 129 meet. The body further comprises a spring 12 which is disposed between the finger receiving portions 142a and 142b and is arranged to bias the actuation member 140, and therefore the tips 20 towards the open position of FIGS. 5 and 6b.

An electrical activation switch 154 (which may for example be a micro switch or a membrane switch) is provided within the body 110 and is positioned between the moveable portions of the actuation member 140. Alternatively, the electrical activation switch 154 could, for example, be positioned between the moveable tips 120. In the illustrated embodiment, the activation switch 154 is connected to one of the finger receiving portions 142a and the other finger receiving portion 142b is provided with an inwardly projecting switch engagement member 153. Thus, as seen in FIG. 6, the activation switch 154 is automatically engaged when the user squeezes the actuation member 140 together so as to close the tips 120. As this embodiment is a bipolar device actuation of the switch 154 enables the RF current to pass through one tip of the device to the other so as to return to the RF generator source (and in doing so passing through and locally heating tissue proximal to or between the tips).

While the invention has been described above with reference to the preferred embodiments, it will be appreciated that various changes or modifications may be made without departing from the scope of the invention as defined in the appended claims.

The invention claimed is:

1. A forceps-type electrosurgical device comprising:
   a fixed elongate body having a substantially hollow profile to define a conduit along a length of the body between a suction port at a forward end of the body and a suction line connection at a rearward end of the body;
   a pair of moveable tips, arranged for engaging tissue in use and extending from a forward end of the body, the tips being relatively moveable between a first position in which the tips are spaced apart and a second position in which the tips are brought together;
   the body further comprising an actuation member moveable relative to the body and connected to the tips such that a user may move the actuation member to result in movement of the tips between the first and second positions;
   wherein the actuation member comprises a pair of finger receiving portions provided on opposing sides of the body; and
   wherein the body comprises a spring disposed between the finger receiving portions inside a structure which extends across the conduit, the spring being arranged to bias the actuation member and tips into the first position.

2. An electrosurgical device as claimed in claim 1, wherein the moveable tips are resiliently biased towards the first position by the elongate body.

3. An electrosurgical device as claimed in claim 1, wherein the actuation member is provided on an outer surface of the elongate body and is inwardly compressible.

4. An electrosurgical device as claimed in claim 1, wherein the suction port is positioned between the tips.

5. An electrosurgical device as claimed in claim 1, further comprising an electrical switch which is activated upon movement of the tips.

6. An electrosurgical device as claimed in claim 5, wherein the electrical switch is engaged by the actuation member.

7. An electrosurgical device as claimed in claim 1, wherein the body further comprises an electrical activation switch on an outer surface thereof.

8. An electrosurgical device as claimed in claim 7, wherein the switch is deactivated when the tips are in the tips are in first position.

9. An electrosurgical device as claimed in claim 7, wherein the switch enables selection between different modes of operation.

10. An electrosurgical device as claimed in claim 1, wherein at least one of the tips comprises an outwardly facing surface with a sharp tapered profile.

11. An electrosurgical device as claimed in claim 10, wherein one of the tips comprises an outwardly facing surface having a blunt profile.

12. An electrosurgical device as claimed in claim 1, wherein the tips comprise inwardly facing opposing planar surfaces.

13. An electrosurgical device as claimed in claim 1, wherein the fixed body is plastic.

14. An electrosurgical device as claimed in claim 13, wherein each tip is a thermally conductive tip.

15. An electrosurgical device as claimed in claim 1, wherein the suction port is positioned on an axial center line of the body.

16. An electrosurgical device as claimed in claim 1, wherein the tips are directly connected to an inner surface of the pair of finger receiving portions.

* * * * *